United States Patent [19]

Uffelman

[11] 4,385,516

[45] May 31, 1983

[54] SYSTEM FOR THE DETECTION OF THE PRESENCE OF A PREDETERMINED CHEMICAL VAPOR DISTRIBUTED IN THE ATMOSPHERE

[76] Inventor: Malcolm R. Uffelman, 1808 Horseback Trail, Vienna, Va. 22180

[21] Appl. No.: 236,061

[22] Filed: Feb. 19, 1981

[51] Int. Cl.[3] .............................................. G01N 29/02

[52] U.S. Cl. .......................................... 73/24; 324/337; 343/5 NA

[58] Field of Search ...................... 73/23, 24; 324/330, 324/335, 337, 344, 58.5 R, 58.5 B; 356/316; 343/5 NA, 5 SA

[56] References Cited

U.S. PATENT DOCUMENTS

| | | | |
|---|---|---|---|
| 2,165,214 | 7/1939 | Blau et al. | 73/23 |
| 3,651,395 | 3/1972 | Owen et al. | 324/337 |
| 3,803,595 | 4/1974 | McMillan | 356/316 |
| 4,100,481 | 7/1978 | Gournay | 324/337 |
| 4,119,950 | 10/1978 | Redding | 73/24 |
| 4,132,943 | 1/1979 | Gournay et al. | 324/335 |

*Primary Examiner*—Stephen A. Kreitman
*Attorney, Agent, or Firm*—John E. Benoit

[57] ABSTRACT

The present invention is a system for the detection of chemical vapors in the atmosphere based on detecting radiation from the molecules of the vapor. The radiation is induced by energy transmitted from the system at a frequency close to an absorption frequency of the molecules of the vapor to be detected. The system provides a easily used means for the excitation and detection of the vapor by virtue of the common tuning control of the system and the direct detection of radiation at the absorption frequency excited by the transmitted energy.

7 Claims, 5 Drawing Figures

SYSTEM FOR THE DETECTION OF THE PRESENCE OF A PREDETERMINED CHEMICAL VAPOR DISTRIBUTED IN THE ATMOSPHERE

BACKGROUND OF THE INVENTION

This invention relates to the detection of chemical vapors distributed in a region of the atmosphere. More specifically, the present invention is a system for the detection of chemical vapors in the atmosphere that directly exploits, in a novel manner, the basic physical principles of quantum mechanical absorption and emission by molecular structures at fixed frequencies determined by the physics of the particular molecular structure. Molecules exhibit the absorption of energy at discrete electromagnetic frequencies due to the quantum effect. Likewise, molecules exhibit emission of energy at discrete frequencies due to the quantum effect. In both absorption and emission, the energy absorbed or emitted is related to the frequency of the absorbed energy or the emitted energy by the fundamental physical constant known as Planks constant, denoted h;

$$\text{Energy} = h \times (\text{frequency})$$

Because of the quantum effect, a particular molecule in isolation will absorb energy at a limited number of fixed discrete frequencies only. These frequencies are known as absorption bands or absorption frequencies. A large number of chemicals have molecular structures having a multiplicity of absorption bands in the microwave frequency region from approximately one Gigahertz ($10^9$ Hertz) to 100 Gigahertz ($10^{11}$ Hertz). It is to these chemicals which may exist as a vapor distributed in the atmosphere that this present invention is addressed. National Bureau of Standards Monograph No. 70, entitled "Microwave Spectral Tables", Volume I through Volume 5, 1968, lists several hundred chemicals having absorption bands in the above mentioned region along with a tabulation of the absorption bands for each of the listed chemicals.

As background to the present invention, the following references are hereby cited:

In 1939, U.S. Pat. No. 2,165,214 was issued to Blau, et al. Blau et al teaches a method for the direct use of absorption band measurements in geophysical prospecting. Blau et al teaches the use of various portions of the electromagnetic spectrum, including light as well as the aforementioned microwave region, to directly measure the absorption frequencies.

In 1972, U.S. Pat. No. 3,651,395 was issued to Owen et al. Owen et al teaches the use of a system which exploits the frequency of radiation from excited hydrocarbon molecules to locate oil and gas deposits. Owen et al teaches the use of the frequency shift that results from highly exciting molecules causing them to emit at a frequency shifted by an amount determined by physics of the molecules from that of the frequency of the exciting energy. This frequency shift physical phenomena is known in the art as Raman Spectroscopy, see "Raman Spectroscopy" by D. A. Long, McGraw Hill, 1977 and, in general, do not correspond to the absorption frequencies.

In 1974, U.S. Pat. No. 3,803,595 was issued to McMillin. McMillin teaches the use of a poly-static system to locate molecules derived from petroleum.

In 1978, U.S. Pat. No. 4,100,481 was issued to Gournay. Gournay teaches a system for detecting and locating hydrocarbon gasses by the means of transmission and reception devices coupled with wide bandwidth and multiple channel narrow band processing devices.

In 1979, U.S. Pat. No. 4,132,943 was issued to Gournay, et al. Gournay, et al teaches an improvement over Gournay to determine the magnitude of the concentration of the hydrocarbon gas.

SUMMARY OF THE INVENTION

Figure 1:
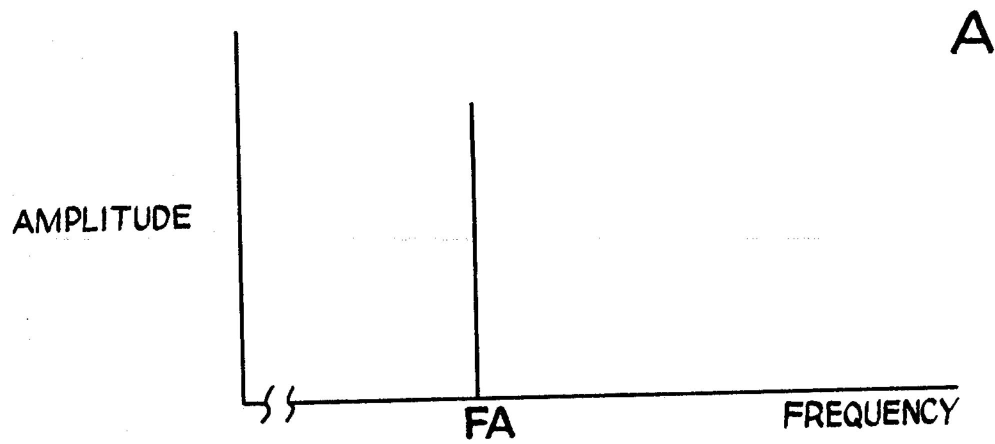
FIG. 1 depicts graphs of the absorption and emission bands for a typical chemical vapor and reveals the basic system approach of this invention for exploiting the physical phenomena.
Figure 1:
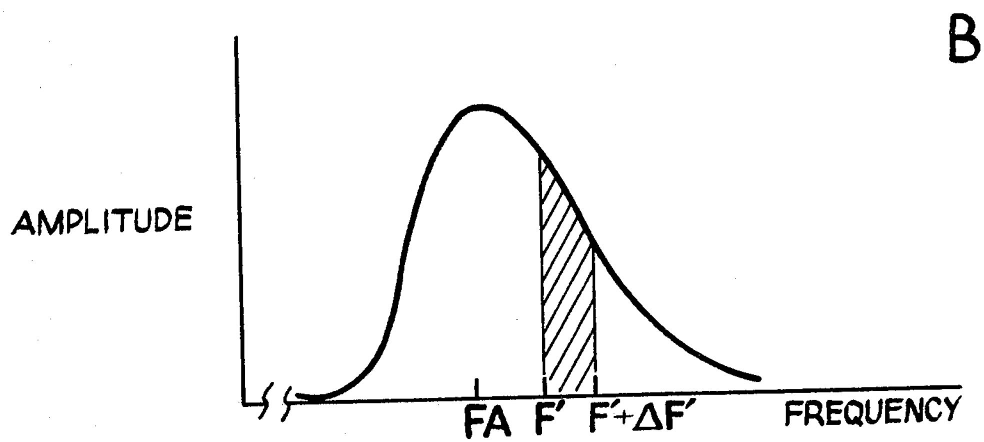
Figure 1:
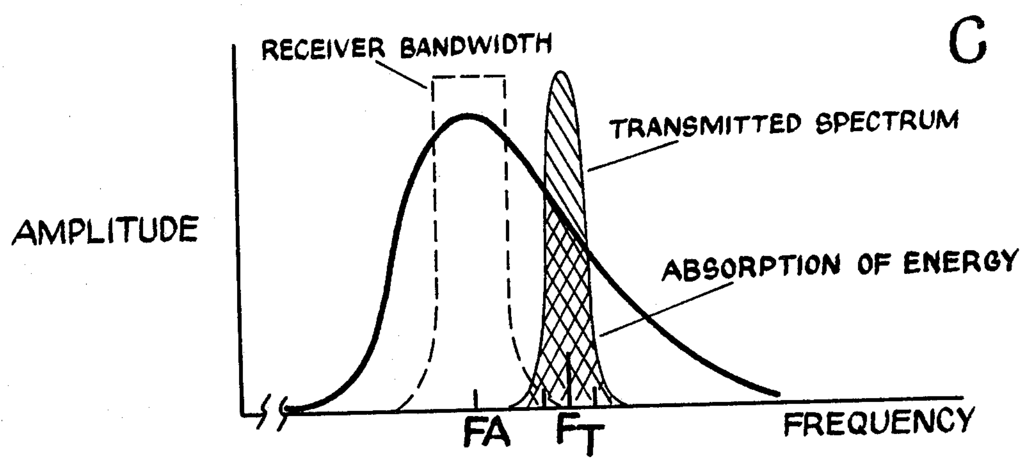

In order to adequately summarize the present invention, it is necessary to examine the physical theory that underpins the invention. In FIG. 1(A), a graph of a typical absorption frequency for a given molecule in isolation is shown. For example, if the chemical is Ketene, the frequency of absorption, denoted FA, shown in FIG. 1(A), can be either 8521.5 MHz, 9188.2 MHz or 9562.7 MHz. In general, a predetermined chemical will have a multiplicity of absorption bands. In the present invention one of the multiplicity of absorption bands is selected for use. In effective isolation (i.e., at low pressure and with molecules from no other chemicals present), the bandwidth of the absorption frequency as show is extremely narrow. In other words, the molecules will absorb energy only if it is almost exactly at the absorption frequency, FA. However, if the molecules are under pressure (such as that of the normal atmosphere) in the presence of other vapors (such as the Oxygen and Nitrogen of the normal atmosphere), the absorption band broadens as shown in FIG. 1(B). The broadened absorption band shape can be interpreted as a probability density function showing the proportion of molecules of the given chemical under pressure that will absorb energy in any given frequency region $F'$ to $F'+\Delta F'$.

Once the energy is absorbed, the normal energy distribution of the molecules, determined in part by the ambient pressure and temperature, is changed. The excited molecules will then tend to redistribute themselves into their normal ambient energy levels. In doing so, they will also radiate the absorbed energy in a band of frequencies according to the distributions shown in FIG. 1(B). Notice that the bulk of the energy will be emitted in the frequency region around FA, the absorption frequency of the isolated molecule.

The present invention provides a system to take maximum advantage of the basic physical laws described above. Transmission of energy is provided at a frequency $F_t$, offset from FA, one of the absorption frequencies of the chemical vapor selected for detection, by an amount $F_o$. The offset frequency $F_o$ is selected to place the transmission frequency $F_t$ as close to FA as possible, to maximize absorption, without causing the transmitted spectrum to unduly overlap the receiver bandwidth (see FIG. 1(C)). The exact value of $F_0$ is not critical in that it does not control or affect the value of FA; that is to say, FA has a fixed value determined by the molecular structure of the selected chemical vapor and is not a shift in frequency as in Raman spectroscopy. The bandwidth of the receiver is established to be wide enough to span the peak of the broadened absorption band to maximize the received energy. The receiver bandwidth spans the frequency region around FA as shown in FIG. 1(C).

An object of the present invention is to provide a controlled, tunable system for the selective detection of each of a multiplicity of predetermined chemical vapors in the atmosphere.

A further object of the present invention is to provide a novel and improved means to remotely detect the presence of a given chemical vapor in a region of the atmosphere.

A further object of the present invention is to provide an improved means to detect the presence of gas and oil deposits through the detection of hydrocarbons in the atmosphere indicative of subsurface deposits of oil or gas.

A further object of the present invention is to provide a novel means to detect leaks in the transmission and distribution systems for natural gas.

A further object of the present invention is to provide a means to detect predetermined polluting chemical vapors in the atmosphere.

The key advantages of the present invention are the single means for tuning control and the direct measurement of the selected absorption frequency by means of a single channel, narrowband device.

The foregoing and other objects, features and advantages of the invention will be better understood from the following detailed description.

DESCRIPTION OF THE PREFERRED EMBODIMENTS

Figure 2:
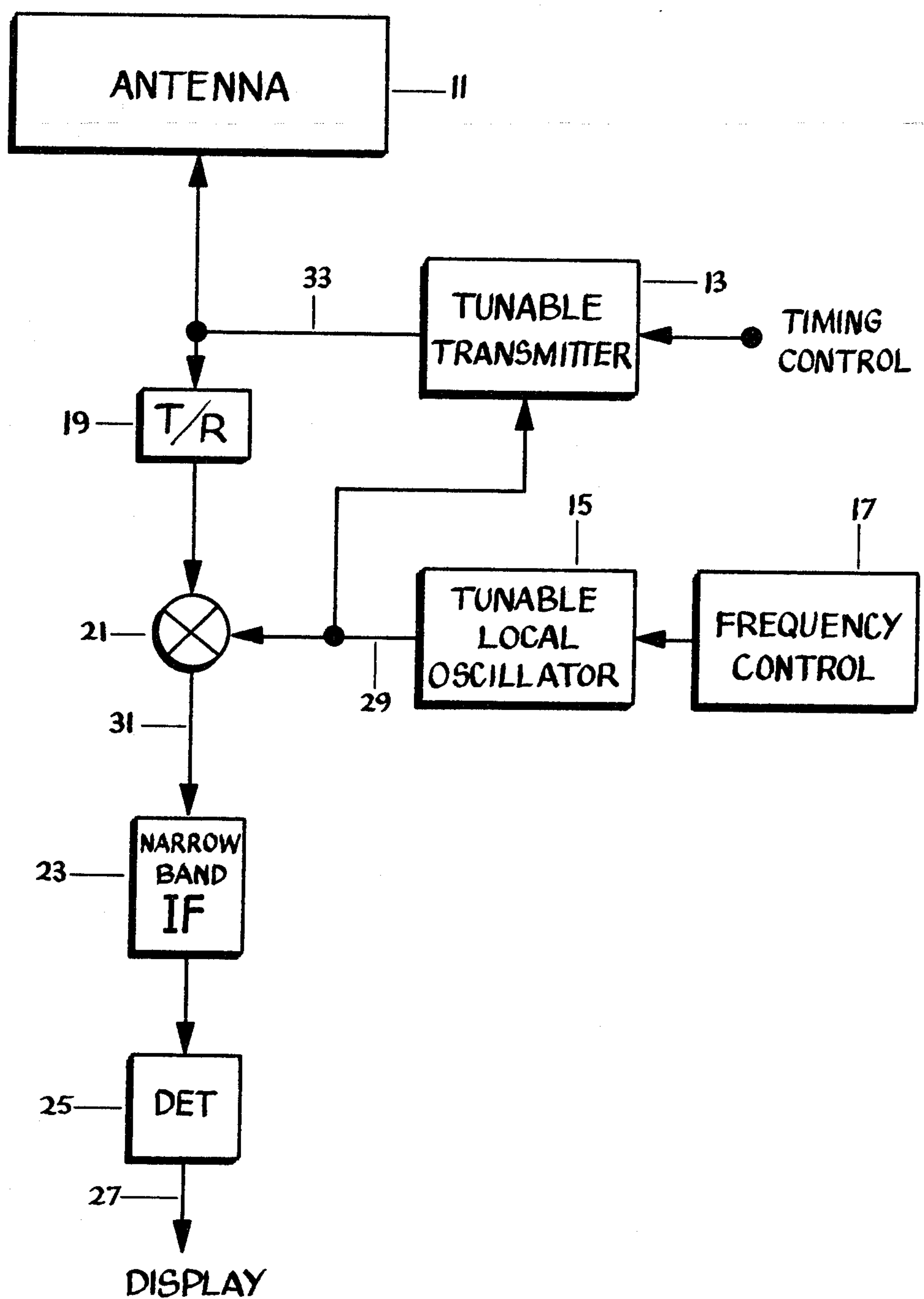
FIG. 2 depicts the block diagram of the invention for the detection of chemical vapors in the atmosphere.

The function and operation of the present invention can be understood by reference to FIG. 2. Before beginning a detailed description of the function and operation of the invention, however, the following terms require definition:

FA is the frequency of the selected absorption band of the predetermined chemical vapor to be detected Fif is the tuned frequency of narrowband IF 23 in FIG. 2, a design parameter normally in the convenient range 1 to 80 MHz Flo is the local oscillator frequency and is tuned to $Flo=FA-Fif$, therefore $Fif=FA-Flo$ (alternatively Flo can be $Fif+FA$; the firm requirement is that $Fif=|FA-Flo|$)

Ft is the transmit frequency and is selected so that $Ft=FA+Fo$ (Ft will later be further defined)

Fo is the offset frequency and is defined by $Fo=Fd-Fif$

Fd is the transmitter delta frequency such that $Ft=Flo+Fd=FA+Fo$, i.e., $Fd=Fo+Fif$ In operation, an absorption band of the chemical vapor to be detected is selected (for example, from NBS monograph 70) and the frequency of the selected absorption band, now denoted FA, is inserted into Frequency Control 17. Frequency Control 17 causes Tunable Local Oscillator 15 to produce a signal on Conductor 29 having a frequency Flo, the difference between FA and Fif. The signal on Conductor 29 is coupled to Tunable Transmitter 13, causing it to produce a pulsed output signal having a frequency Ft on Conductor 33. The signal on Conductor 33 is coupled to Antenna 11 and from there radiated into the atmosphere. Antenna 11 is a directional antenna capable of directing the radiated signal in a desired direction and consequently causing the emitted energy to be directed to the region of the atmosphere to be investigated. Transmit-Receive Switch 19 prevents the high energy pulse produced by Transmitter 13 from entering Mixer 21. The action of Transmit-Receive Switch 19 is well known in the art and is discussed in "Introduction to Radar Systems" by M. Skolnik, McGraw Hill, 1962. The pulsed signals produced by Transmitter 13 are normally periodic in nature; however, periodicity is not a necessary condition for the operation of the invention; the pulses may occur in an aperiodic fashion. Further, the pulse rate may be established by an external timing control without deviating from the intent of the invention. The function of an exterior timing control will be discussed herein in a later portion of this specification. Tunable Local Oscillator 15, Tunable Transmitter 13, Antenna 11, and the action of TR Switch 19 in conjunction with their indicated interconnections form a tunable transmitting means for directing transmitted energy at the region of the atmosphere to be investigated.

During the periods in which pulsed signals are not being transmitted, Antenna 11 receives electromagnetic energy from the region of the atmosphere upon which it is directed. These signals are coupled to Transmit-Receive Switch 19 and are thereby passed to Mixer 21. The action of Mixer 21 is to produce an output signal on Conductor 31 whose frequency is the difference between the frequency FA of the received signal and the frequency Flo of the output of Local Oscillator 15 which is coupled on Conductor 29 to Mixer 21. Said signal on Conductor 31 is coupled to Narrow Band IF 23. Narrow Band IF 23 is a tuned amplifier having a pass band around the tuned frequency such as to pass only signals in the frequency region of a signal resulting from signals with frequency in the region of FA received at Antenna 11. In other words, if the predetermined chemical vapor is present in a region of space upon which the transmitted energy is directed, the chemical vapor will emit signals in the region around the frequency FA as shown in FIG. 1(C). In this case, the signals appearing on Conductor 31 are, as defined herein above, in the region around, FA - Flo. Consequently, signals resulting from the reception at Antenna 11 of signals in the frequency region indicative of the presence of the predetermined chemical vapor will be amplified by Narrow Band IF 23. The output of Narrow Band IF 23 is coupled to Detector 25. The function of Detector 25 is to produce a signal indicative of the power contained in the received signal. The design of detectors of this type, such as square law detectors, is well known in the electronic art. There are a number of different, conventional and well known detectors which can be used without deviating from the spirit or intent of this invention. The signal produced by Detector 25 is then coupled in Conductor 27 to one of a number of appropriate display devices. Any number of conventional display devices, such as an oscilloscope, strip recorder, voltage meter, audible indicator or other well known displays can be used. One such conventional display can be the well known Planned Position Indicator, or as it is called in the art, "The PPI Radar Display". Displays of this type require synchronization with the transmitting function to produce a coherent display. In cases where such displays are to be used, the timing control indicated in FIG. 2 would be used for synchronization.

Antenna 11, Transmit-Receive Switch 19, Mixer 21, Narrow Band IF 23, Detector 25, Tunable Local Oscillator 15, and their associated inter-connections form a tunable receiving means which can be directed at the desired region of the atmosphere to be investigated for the presence of the predetermined chemical vapor.

Frequency Control 17 provides a simple and direct means to tune the system of FIG. 2 to detect the presence of the desired predetermined chemical vapor. Frequency control 17 is coupled to the Transmitting means and to the Receiving means by its control of Tunable Local Oscillator 15, a component of both the transmitting and the receiving means.

The present invention has several advantages over the prior art as can be readily understood from the description of the system as depicted in FIG. 2. The following are some of the key advantages of the present invention: The system as depicted in FIG. 2 directly detects the presence of a chemical vapor in accordance with the established laws of Physics from a single location. A single means is provided for tuning control of the transmitting and receiving means so that the system can be quickly and directly tuned to detect the presence of the desired predetermined chemical vapor. The present invention provides a means to detect the predetermined chemical vapor by exciting and detecting an absolute frequency emission, FA, of the chemical vapor and does not depend upon detection of relative frequencies or frequency shifts as taught by Owens et al. The receiving means of the present invention directly detects signals in the frequency region of the absorption band and does not require wide band and multiple, narrow band processing for detection as taught by Gournay.

Figure 3:
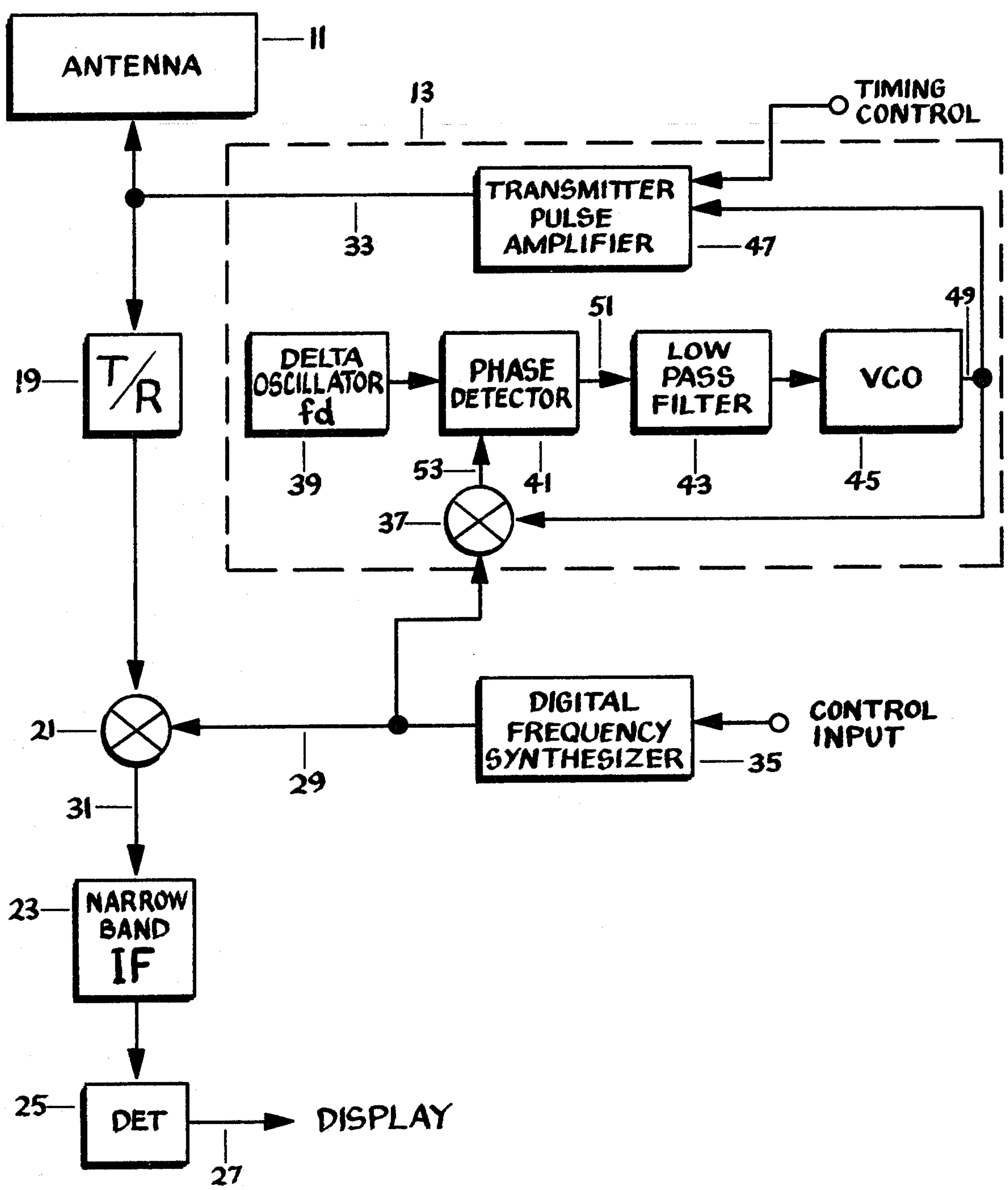
FIG. 3 depicts a detailed block diagram for a preferred embodiment of the invention.

FIG. 3 shows the details of a specific embodiment of the system depicted in FIG. 2, for use when a large number of chemical vapors are of interest. Antenna 11, Transmit-receive Switch 19, Mixer 21, Narrow Band IF 23, and Detector 25 function and provide the same operational features as described in conjunction with FIG. 2. As shown in FIG. 3, Tunable Transmitter 13 comprises Transmitter Pulse Amplifier 47, Voltage Control Oscillator 45, Low Pass Filter 43, Phase Detector 41, Delta Oscillator 39, and Image Rejection Mixer 37. The theory and practice of image rejection mixers is discussed in "Radar Handbook" by M. Skolnik, McGraw Hill, 1970 (see page 10 of Chapter 5). An image rejection mixer is required to prevent the incorrect sideband from causing the transmitter to tune to the wrong value of frequency. Image Rejection Mixer 37, Phase Detector 41, Low Pass Filter 43 and Voltage Coantrol Oscillator 45 along with their associated interrconnections form a phase locked loop. The action of the phase locked loop and the associated Delta Oscillator 39 are as follows. Local Oscillator signal Flo on Conductor 29 is mixed in Mixer 37 with the signal on Conductor 49 produced by Voltage Control Oscillator 45. The output of Mixer 37 on Conductor 53 is the difference between the frequency of the output of Voltage Control Oscillator 45 and Local Oscillator signal Flo on Conductor 29. This difference signal on Conductor 53 is coupled to Phase Detector 41. The output of Delta Oscillator 39 is also coupled to Phase Detector 41. The frequency of the signal produced by Delta Oscillator 39 is Fd, as defined previously herein. The output of Phase Detector 41 which appears on Conductor 51 is a voltage proportional to the phase difference between the local oscillator signal Flo on Conductor 29 and the Voltage Control Oscillator signal on Conductor 49. The signal on Conductor 51 is passed through Low Pass filter 53 which acts as a leaky integrator to smooth the phase difference signal produced by Phase Detector 41. The output of Low Pass Filter 43 is used to control Voltage Control Oscillator 45. The frequency of the signal produced by Voltage Control Oscillator 45, under control of the signal of Low Pass Filter 43, is proportional to the voltage of the output of Low Pass Filter 43. The action of the phase locked loop is similar to a servo mechanism loop in that when the phase of the signal on Conductor 53 produced by Mixer 37 and the phase of the output of Delta Oscillator 39 are equal, the loop is in the lock condition and the frequency of the signal produced by Voltage Control Oscillator 45 is equal to Flo+Fd. As defined previously herein, Flo+Fd is equal to FA+Fo which is in turn equal to Ft, the desired transmitting frequency. The output of Voltage Control Oscillator 45 is coupled to Transmitter Pulse Amplifier 47. Transmitter Pulse Amplifier 47 uses the Voltage Control Oscillator 45 output on Conductor as its transmitting reference signal and produces amplified pulses of the same frequency on Output Conductor 33. The timing of the pulses can be controlled either through an external timing control as shown in FIG. 3 or by means of an internal oscillator control.

The function of Tunable Oscillator 15 and Frequency Control 17 depicted in FIG. 2 are provided in the embodiment of FIG. 3 by a Digital Frequency Synthesizer 35 and its control input. There are commercially available frequency synthesizers such as the Hewlett-Packard Model HP8672A which will perform the function required by Digital Frequency Synthesizer 35. When using a direct frequency synthesizer, such as the HP8672A, the frequency is inserted by means of the device's input control panel, thereby providing the function of Frequency Control 17 of FIG. 2.

Figure 4:
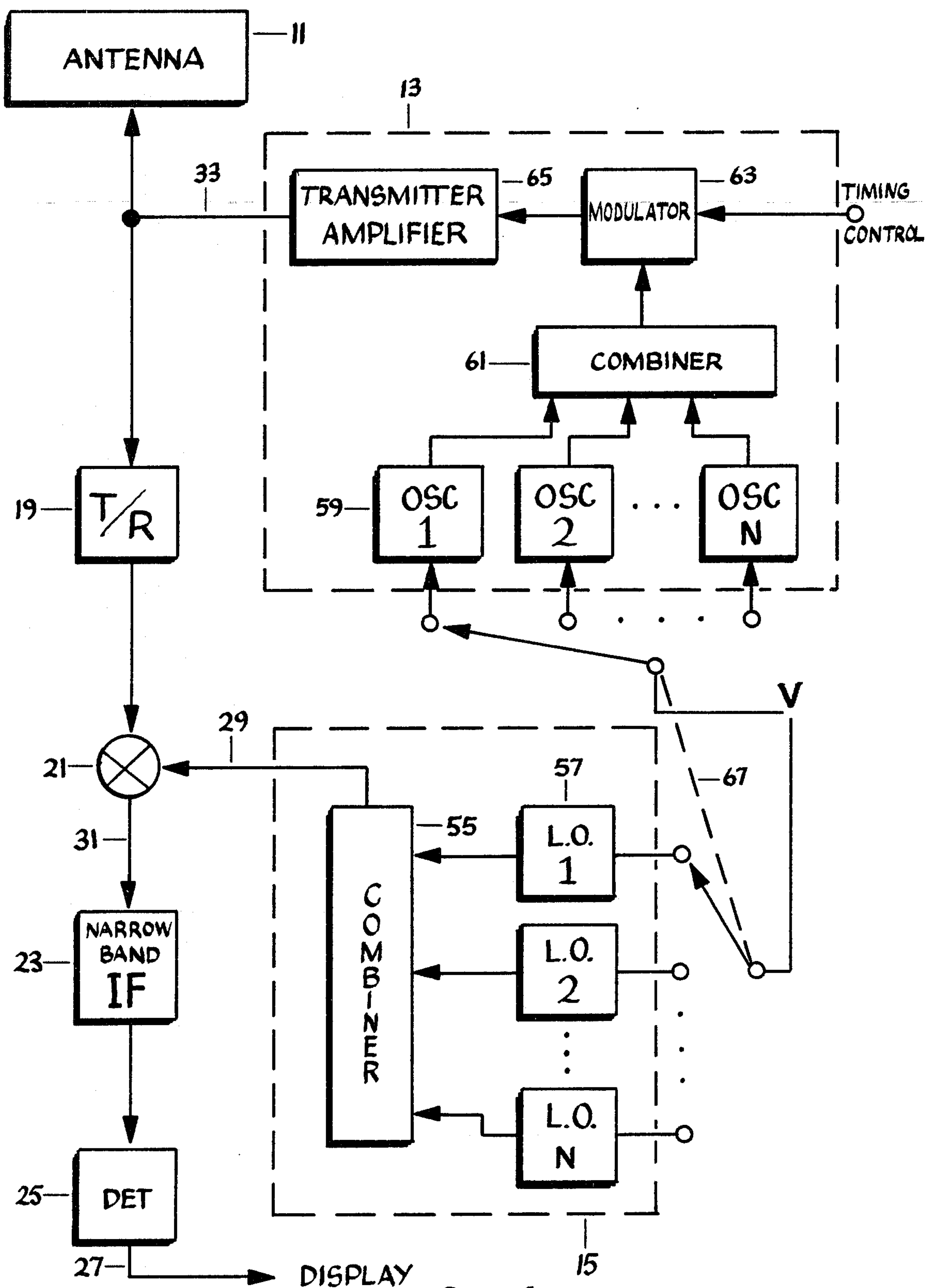
FIG. 4 depicts an alternative embodiment for the present invention.

FIG. 4 depicts a detailed block diagram of an alternate embodiment of the present invention. This alternate embodiment as depicted in FIG. 4 is particularly useful when there are a limited number of predetermined chemical vapors of interest. Again, Antenna 11, Transmit-Receive Switch 19, Mixer 21, Narrow Band IF 23, and Detector 25 serve the same functions as previously described herein. Tunable Local Oscillator 15 comprises Combiner 55 and a multiplicity of individual local oscillators 57. Since the utility of the system depicted in FIG. 4 is in cases where there are a limited number of chemical vapors of interest, a limited number of local oscillators set at the appropriate Flo suffice; therefore, there will be one local Oscillator 57 for each of the chemical vapors of interest, tuned to the appropriate frequency for detecting the appropriate absorption band associated with the given chemical vapor. The outputs of Local Oscillators 57 are coupled to Combiner 55 which produces the selected output Flo on Conductor 29.

Tunable Transmitter 13 comprises Transmitter Amplifier 65, Modulator 63, Combiner 61 and Oscillators 59. Each of the multiplicity of Oscillators 59 is tuned to produce the required frequency Ft for the individual chemical vapors of interest. The outputs from Oscillators 59 are coupled to Combiner 61 which produces as its output the selected signal from the selected one of Oscillators 59. The output from Combiner 61 is coupled to Modulator 63 which in conjunction with the timing control input produces pulses of frequency Ft. The output of Modulator 63 is coupled to Transmitter Amplifier 65 which amplifies the pulses produced by Modulator 63 and couples these to Antenna 11 on Conductor 33.

Multiple-ganged Switch 67 provides the function of Frequency Control 17 described in FIG. 2. Thus, through the use of Switch 67 the system can be controlled to produce the desired transmit frequency Ft and to receive and to detect signals at the desired frequency FA.

It is possible to have an alternate definition of Ft consistent with the functioning of the invention as defined herein above in relation to FIG. 1, FIG. 2, FIG. 3, and FIG. 4. The alternate definition for Ft is that Ft is equal to FA minus Fo. It can be readily seen from FIG. 1 that the transmit frequency Ft can also be lower in frequency than Fa and still cause absorption of energy by the molecules of the chemical vapor. Again, according to the Physical Laws of absorption and emission of chemical vapors under pressure, the emission of energy will be distributed in frequency according to the curve shown in FIG. 1(B). In other words, the significant portion of defining Fo is that its magnitude be such that Ft is close to FA, but sufficiently displaced such that Ft does not overlap the frequency region set by the receiving means bandwidth shown in FIG. 1. Thus, given the magnitude of Fo, the value of Ft can be now defined as FA±Fo or in mathematical terms as the algebraic sum of FA and Fo; where the magnitude of Fo is set but its sign can be arbitrarily selected.

The system embodiments of the present invention as depicted in FIG. 2 and described in detail in FIG. 3 and FIG. 4 all employ pulsed emissions to excite the molecules of the predetermined chemical vapor. The advantage of using pulsed emissions is that greater transmitted power can be achieved and consequently greater detection ranges can be achieved than those possible if continuous waves or CW transmissions were used.

However, there are disadvantages associated with pulse transmissions. The ideal frequency power spectrum of a periodic train of rectangular RF pulses has the form $$\frac{\sin \pi}{fT/\pi ft}$$

where f is the RF frequency and T is the width of the pulse. Examination of this function reveals that as T, the width of the pulse becomes smaller (i.e., narrow pulse width) the spectrum emitted spreads in frequency around the transmitted frequency f. Spreading of the spectrum causes interference with the detection of emission from the chemical vapor under investigation (refer to FIG. 1(*c*)). Therefore, wider pulses are desired to reduce the spread of transmitted energy into the receiver passband. In general, pulses with widths in the order of one to two microseconds are desirable to allow a small value of Fo without creating large interference at FA. Transmit-receive Switch 19 closes off the receiving function during the pulse transmission. Thus, it can be seen that a blind zone exists for a minimum of one-half the pulse width. Further, after the cessation of the pulse, Transmit-receive Switch 19 has a recovery period before reception can begin that is generally in the order of one to two microseconds. The resulting blind region for a one microsecond pulse is a radius around the antenna of approximately one quarter of a nautical mile or about 1500 feet. In high power pulse systems intended for wide areas (i.e., long ranges) use, this is a minor disadvantage. However, in some applications (e.g., searching for leaks in natural gas distribution systems, or analyzing pollution vapors in a confined area) this can be a serious disadvantage. This disadvantage can be overcome some what in a pulse system through the use of a circulator to couple Tunable Transmitter 13 and Mixer 21 to Antenna 11. The use of circulators in this application are well known in the art and is adequately discussed in "Radar Handbook" by M. Skolnik, McGraw-Hill, 1970, Chapter 8. This approach does limit, however, the peak power that can be emitted and therefore limits the range of the system. The embodiment of the present invention depicted in FIG. 5 overcomes the disadvantage of a blind region by the use of continuous wave, referred to as C.W., transmission rather than pulse transmission. The use of a C.W. mode of operation as an alternative embodiment of the present invention requires further definitions. In the C.W. embodiment of FIG. 5, $$Fif=fo$$

$$Flo=Ft$$

and as before, $$Ft=FA+Fo$$

or $$Ft=FA-Fo$$

(i.e., Ft is the algebraic sum of FA and Fo).

Figure 5:
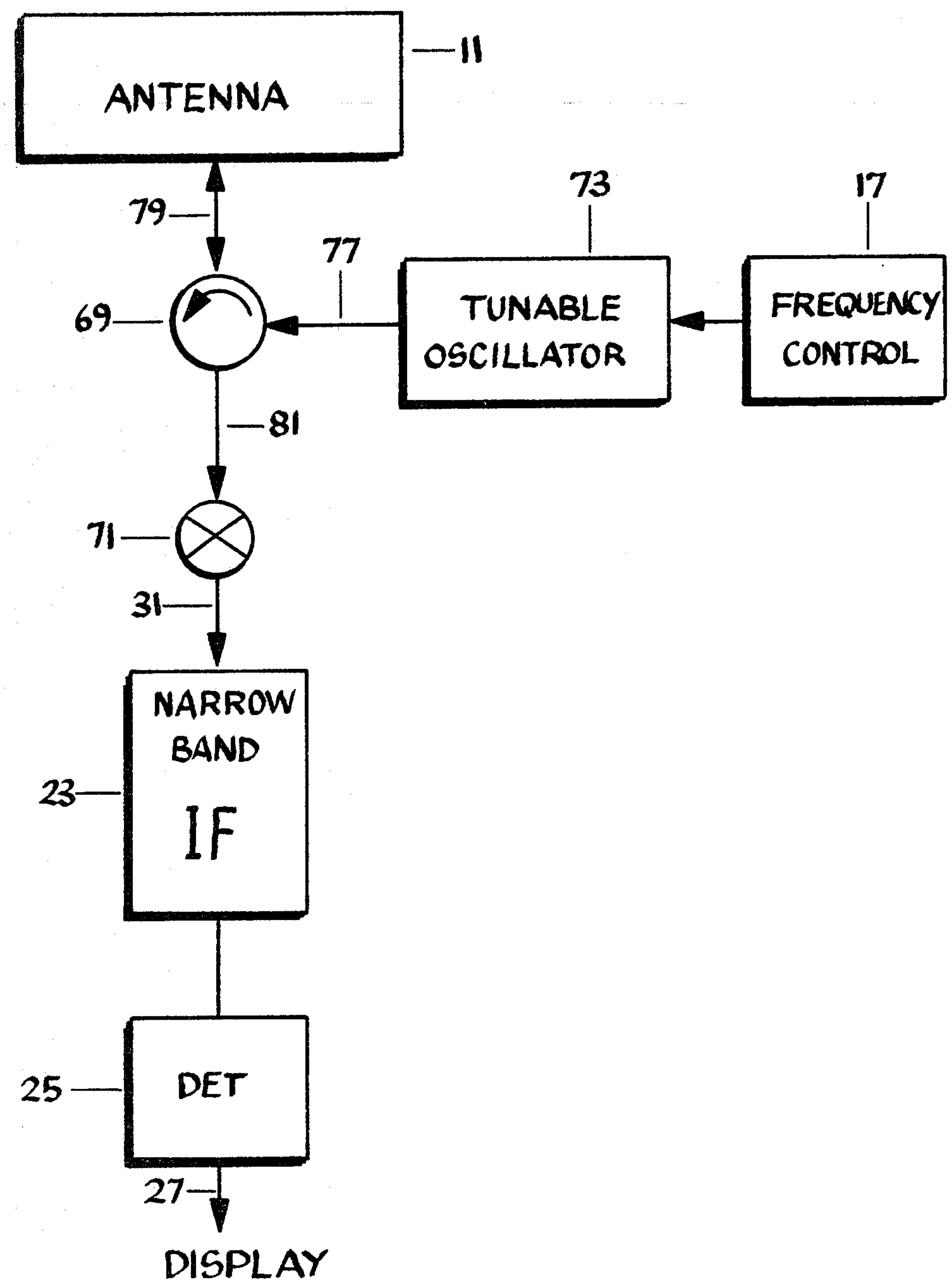
FIG. 5 depicts an alternative embodiment of the invention for use with continuous wave transmission.

The following description of the embodiment depicted in FIG. 5 will assume Ft=FA+Fo, however, either the sum or the difference (i.e., the algebraic sum) is within the scope of the present invention.

With reference to FIG. 5, Antenna 11, Narrowband IF 23, and Detector 25 serve the same functions as described above herein. Tunable Oscillator 73 provides a C.W. signal at frequency Ft as defined by frequency Control 17. Tunable Oscillator 73 produces output signal on Conductor 77. Conductor 77 couples output of Tunable Oscillator 73 to Circulator 69. The action of Circulator 69 is to couple the signal on Conductor 77 to Conductor 79 but not to Conductor 81. Conductor 79 couples the signal produced by Tunable Oscillator 73 to Antenna 11. Thus, Tunable Oscillator 73, Circulator 69, and Antenna 11, together with conductors 77 and 79 comprise a tunable transmitting means. Signals received by Antenna 11 are coupled to Circulator 69 by means of Conductor 79. The action of Circulator 69 is to couple signals from Antenna 11 on Conductor 79 to Conductor 81, but not to Conductor 77. Conductor 81 couples the received signals to Mixer 71. To perform the mixing function, Mixer 71 requires not only the signal to be heterodyned but a local oscillator signal. Because small missmatches of impedance always occur at junctions, some of the signal at frequency Ft produced by Tunable Oscillator 73 is reflected from the junction of Antenna 11 and Conductor 79. In practice, it is often necessary to deliberately increase the impedance missmatch to provide sufficient reflection. The reflected signal is coupled by Circulator 69 to Mixer 71 by way of Conductor 81, thereby providing the second signal needed for the heterodying operation. The output of Mixer 71 is coupled to Narrowband IF 23 by means of Conductor 31. If a signal having energy in the region around FA is received by Antenna 11, Narrowband IF 23 will produce an output in the pass band of Narrowband IF 23. This output of Narrowband IF 23 is coupled to Detector 25 as described hereinabove.

By the functions described in the previous paragraphs, it can be seen that Antenna 11, Circulator 69, Tunable Oscillator 73, Mixer 71, Narrowband IF 23, and Detector 25 along with their interconnections comprise a tunable receiving means. Frequency Control 17 is coupled to the tunable transmitting means and to the tunable receiving means through its effect on Tunable Oscillator 73.

The output of Detector 25 maybe be coupled to one or more forms of display devices by means of Conductor 27 without departing from the intent of the present invention.

While specific embodiments of the present invention have been shown and described, other modifications are within the spirit and scope of the invention; therefore, the invention is limited only by the following claims.

What is claimed is:

1. A system for detecting the presence of a predetermined chemical vapor distributed in a region of the atmosphere comprising tunable pulse signal transmitting means directed at said region of the atmosphere;

tunable single channel, narrowband receiving means directed at said region of the atmosphere;

control means coupled to said tunable transmitting means for tuning said transmitting means so as to emit a pulsed signal having a frequency Ft equal to the algebraic sum of predetermined frequency FA and offset frequency Fo;

said control means further coupled to said tunable receiving means for tuning said receiving means so as to receive signals having frequencies only in the region around said predetermined frequency FA; and display means coupled to said tunable receiving means for indicating the reception of said signals having frequencies in the region around said predetermined frequency FA.

2. The system of claim 1 wherein said tunable pulse transmitting means comprises a directional antenna coupled to a tunable transmitter.

3. The system of claim 1 wherein said tunable single channel, narrowband receiving means comprises a mixer;

a directional antenna coupled to said mixer via a transmit/receive switch;

a tunable local oscillator coupled to said mixer; and a single narrowband IF amplifier tuned to amplify signals in the frequency region around FA-Flo coupled to said mixer.

4. A system for detecting the presence of a predetermined chemical vapor distributed in a region of the atmosphere comprising tunable continuous wave transmitting means directed at said region of the atmosphere;

tunable receiving means directed at said region of the atmosphere;

control means coupled to said tunable transmitting means for tuning said transmitting means as to emit a continuous wave signal having a frequency Ft equal to the algebraic sum of predetermined frequency FA and offset frequency Fo;

said control means further coupled to said tunable receiver means for tuning said receiving means so as to receive signals having frequencies in the region around said predetermined frequency FA; and display means coupled to said tunable receiving means for indicating the reception of said signals having frequencies in the region around said predetermined frequency FA.

5. The system of claim 4 wherein said transmitting means comprises a tunable continuous wave oscillator coupled to a circulator; and a directional antenna coupled to said circulator whereby the signal produced by said oscillator is coupled to said antenna.

6. The system of claim 4 wherein said receiving means comprises a directional antenna coupled to a circulator;

a mixer coupled to said circulator; and a narrowband IF amplifier coupled to said mixer.

7. The system of claim 4 further comprising a mixer; and means for providing a reflected signal to said mixer.

* * * * *